United States Patent [19]

Griffith et al.

[11] Patent Number: 4,578,508

[45] Date of Patent: Mar. 25, 1986

[54] FLUOROACRYLATE ESTER, POLYMER THEREOF, AND PROCESS OF MAKING THE SAME

[75] Inventors: James R. Griffith, Riverdale Heights; Jacques G. O'Rear, Temple Hills, both of Md.

[73] Assignee: Geo-Centers, Inc., St. Newton Upper Falls, Mass.

[21] Appl. No.: 705,880

[22] Filed: Feb. 26, 1985

[51] Int. Cl.$^4$ ............................................. C07C 69/52
[52] U.S. Cl. .................................................. 560/221
[58] Field of Search ......................................... 560/221

[56] References Cited

PUBLICATIONS

"Umbrella Fluoroacrylic Polymers": Griffith, James R.: Chemical Abstracts 101: 23971k.

Primary Examiner—Paul R. Michl
Assistant Examiner—Alex H. Walker
Attorney, Agent, or Firm—Wolf, Greenfield & Sacks

[57] ABSTRACT

A fluoroacrylate ester monomer having the formula:

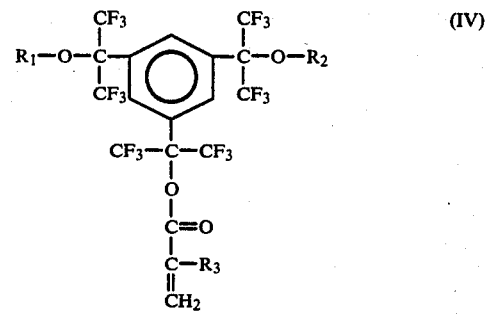

wherein $R_1$ and $R_2$ are independently selected from the group consisting of saturated aliphatic hydrocarbons having from 1 to about 3 carbon atoms and $R_3$ is selected from the group consisting of hydrogen and methyl. The monomer has a water-repellent "umbrella" of 3 gem bis trifluoromethyl groups around the acrylate monomer which do not interfere with the acrylate properties. Polymerization of the monomer results in a stable, exceptionally hydrophobic, linear thermoplastic polymer. The invention also includes processes for making the monomer from a diether halide and certain novel intermediates.

8 Claims, No Drawings

FLUOROACRYLATE ESTER, POLYMER THEREOF, AND PROCESS OF MAKING THE SAME

U.S. GOVERNMENT RIGHTS IN THE INVENTION

This invention was made in the performance by Geo-Centers, Inc., of work under Naval Research Laboratory contract N00014-83-C-2177. The United States of America has certain rights in the invention arising out of its support of that work.

FIELD OF THE INVENTION

This invention relates to fluoropolymers and in particular to hydrophobic fluorinated acrylic polymers and to a process of making the same.

BACKGROUND OF THE INVENTION

Some years ago it was shown by Shafrin and her co-workers that a field of close-packed trifluoromethyl groups has an extremely low critical surface tension of only 6 dynes/cm. This was surprising in view of the fact that chains of difluoromethylene groups, as found in polytetrafluoroethylene, have a critical surface tension of 18 dynes/cm. E. G. Shafrin et al., "Constitutive Relations In The Wetting of Low Energy Surfaces And The Theory Of The Retraction Method Of Preparing Monolayers," 64 J. Phys. Chem. 519–524 (1960).

Various attempts have been made to produce acrylic polymers having trifluoromethyl groups. U.S. Pat. No. 3,544,535 (Gilbert et al.) describes the production of 2-(pentafluorophenyl)hexafluoroisopropanol by the reaction of pentafluorophenyl magnesium bromide with hexafluoroacetone in an ether solvent followed by hydrolysis of the reaction product. The acrylate and methacrylate esters are prepared by reacting 2-(pentafluorophenol)hexafluoroisopropanol with an acrylic compound in an organic solvent and in the presence of an adjuvant such as triethylamine. Polymerization of the acrylate and methacrylate esters is accomplished in the presence of a catalyst such as potassium persulfate or benzoyl peroxide. The polymers are said to have hydrophobic properties and to be useful as textile impregnants.

U.S. Pat. Nos. 4,356,296 and 4,452,998 to Griffith et al. describe the synthesis and polymerization of a fluorinated diacrylate ester monomer having the formula:

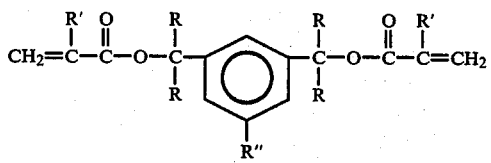

wherein R is —CF₃ or —C₂F₅, R' is —H or —CH₃, R" is —H or —(CF₂)ₙF, and n is an integer of from 1 to 10. The monomer is prepared by reacting a fluoroaromatic diol and acryloyl chloride in a highly fluorinated solvent and in the presence of an acid acceptor. The monomer forms a hydrophobic cross-linked thermoset polymer having dental and biomedical applications. See also U.S. Pat. No. 4,284,747 (Griffith et al.).

U.S. Pat. No. 3,407,183 (Farah et al.) concerns the production of the acrylate and methacrylate esters of 1,3-bis(heptafluoroisopropyl)benzenesulfonyl-(N-alkyl,N-2-hydroxyethyl) amides. The polymers of these esters are said to be useful for treating fabrics to render them oil repellant.

U.S. Pat. No. 3,304,334 (Jones) describes the production of tris-1,3,5-(2-hydroxyhexafluoro-2-propyl) benzene by reacting bis-1,3-(2-hydroxyhexafluoro-2-propyl) benzene with hexafluoroacetone in the presence of BF₃ and at a pressure of 20 kilobars. The product was found to be hygroscopic and was said to be useful as a reactant in the preparation of polyethers, polyesters, polyamides, and polyurethanes, as plastics, fibers, coatings, elastomers, and foams, and because of its tri-functionality, as a cross-linking agent when used in small amounts in the preparation of polymers. When reacted with 2,4-toluene diisocyanate a polymer having high electrical resistivity and good dielectric properties is said to be produced.

SUMMARY OF THE INVENTION

It is an object of this invention to provide a water-repellent "umbrella" of 3 gem bis trifluoromethyl groups around an acrylate monomer unit without interfering with the acrylate properties.

Another object is to provide a stable, linear thermoplastic polymer thereof which is exceptionally hydrophobic.

Further objects include novel intermediates and processes for making the monomer, polymer, and intermediates.

The monomer of this invention is a fluoroacrylate ester of the formula:

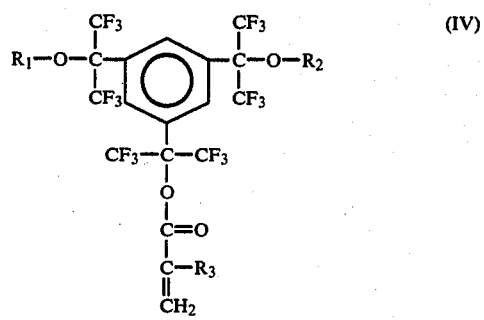

wherein $R_1$ and $R_2$ are independently selected from the group consisting of saturated aliphatic hydrocarbon shaving from 1 to about 3 carbon atoms and $R_3$ is selected from the group consisting of hydrogen and methyl. Preferably $R_1$ and $R_2$ are each methyl and $R_3$ is hydrogen—such that the fluoroacrylate ester is 1,3-bis-(2-methoxyhexafluoro-2-propyl)-5-(2-hydroxyhexafluoro-2-propyl)-benzene acrylate.

The process of the invention for making the monomer (IV) comprises the steps of:

reacting hexafluoroacetone with a first compound of the formula:

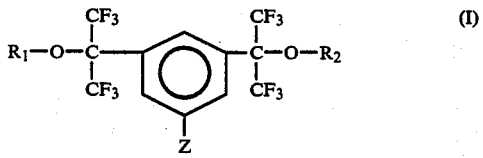

wherein Z is selected from the group consisting of lithium and MgX, where Mg is magnesium and X is a halogen, and hydrolyzing the resulting intermediate with a dilute acid to form a diether ol of the formula:

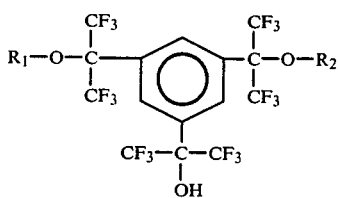

reacting the diether ol with an acrylic compound of the formula:

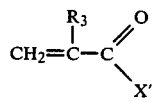

wherein X' is selected from the group consisting of chlorine and bromine, in the presence of an adjuvant and in an inert organic solvent to form the fluoroacrylate ester (IV). Preferably, Z is magnesium iodide, X' is chlorine, the adjuvant is triethylamine, and the solvent is Freon 113.

The invention further includes a novel Grignard reagent, a novel diether ol, and processes for making the same.

The Grignard reagent is prepared by reacting a compound of the formula:

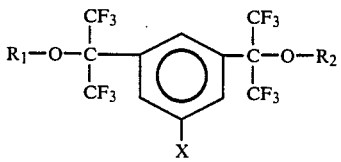

wherein X is a halogen, with magnesium in the presence of an ether solvent and in the absence of water to form:

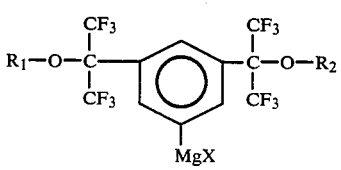

The novel diether ol is prepared from (VI) in the same nammer as previously described for preparing (III) from (II).

The invention further comprises a linear, thermoplastic, and extremely hydrophobic polymer prepared from the fluoroacrylate ester monomer (IV). The preferred polymer has a molecular weight of from about 6,000 to about 60,000. Polymerization is preferably conducted in the presence of a catalyst such as benzoyl peroxide and at a temperature of about 85° C.

Additional features of the invention, its nature and various advantages will be better understood from the following description of the preferred embodiments.

DETAILED DESCRIPTION OF THE PREFERRED EMBODIMENTS

The present invention relates to a novel monomer, its synthesis, and polymerization.

The monomer of this invention has the formula:

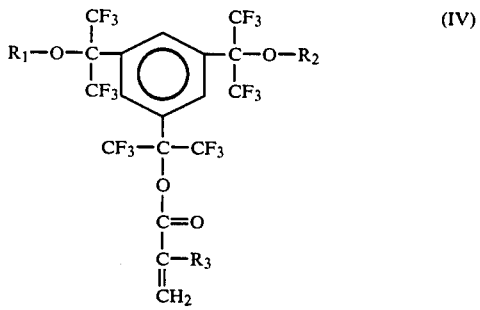

wherein $R_1$ and $R_2$ are independently selected from the group consisting of saturated aliphatic hydrocarbons having from 1 to about 3 carbon atoms and $R_3$ is selected from the group consisting of hydrogen and methyl. The hexagonal symbol containing a circle represents a benzene ring. The 3 gem bis trifluoromethyl groups around the acrylate monomer provide a water-repellent "umbrella" without interfering with the acrylate properties. Preferably $R_1$ and $R_2$ are methyl and $R_3$ is hydrogen.

Polymerization of monomer (IV) results in a stable, exceptionally hydrophobic, linear thermoplastic. The polymer preferably has a molecular weight of from about 6,000 to about 60,000, more preferably of from about 6,000 to about 10,000, and most preferably of from about 6,000 to about 8,000.

Polymerization is preferably conducted in the presence of a catalyst such as benzoyl peroxide, methyl ethyl ketone, peroxide, azodiisobutyronitrile, or similar free radical initiator, or in the presence of a photoinitiator such as benzoin methyl ether. Other preferred polymerization conditions include a temperature of from about 25° to 100° C., an atmosphere of nitrogen, argon, or other inert gas, a pressure of about 1 atmosphere and a time of from about 10 seconds to about 1 hour. Preferably the polymerization is carried out at about 85° C. with benzoyl peroxide as the catalyst.

The hydrophobic nature of the polymer is illustrated by its water contact angle of at least 90° and the ready mobility of water droplets on the polymer surface. The polymer has been prepared in bulk at a temperature of 85° C. with benzoyl peroxide to form a water-clear plastic which was somewhat brittle, soluble in highly fluorinated solvents, and capable of producing films having a 91° water contact angle. Tougher polymers can be produced by polymerization for longer periods of time and using a smaller amount of catalyst.

The polymer is useful in the forms of films, castings, laminates, adhesives and coatings, and in such useful articles as windows, sight glasses, and lenses. The polymer will coat a variety of substrates including metal, wood, and glass. Solutions of the polymer in Freon 113 have been applied to metal substrates and cured by evaporation of the carrier at room temperature. Ultrathin coatings of the polymer on steam condensers have been found to promote and sustain dropwise condensation of steam and enhance heat transfer.

The process of this invention for making the fluoroacrylate ester monomer (IV) comprises the steps of:

reacting hexafluoroacetone with a first compound of the formula:

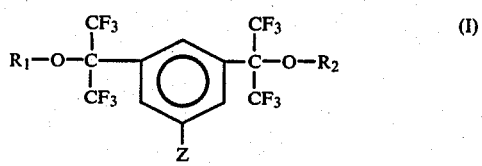

wherein Z is selected from the group consisting of lithium and MgX, where Mg is magnesium and X is a halogen, and hydrolyzing the resulting intermediate with a dilute acid to form a diether ol of the formula:

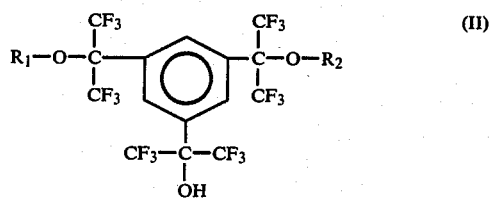

reacting the diether ol with an acrylic compound of the formula:

wherein X' is selected from the group consisting of chlorine and bromine, in the presence of an adjuvant and in an inert organic solvent to form (IV).

The first compound or first intermediate (I) is either a Grignard reagent (Z is MgX) or a lithium derivative (Z is lithium). The Grignard reagent (I) is prepared by reacting a diether halide of the formula:

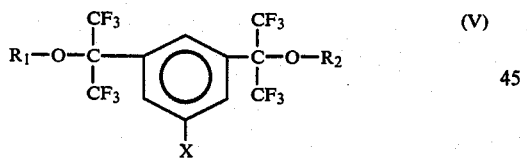

wherein X is a halogen, with magnesium in a mole ratio of from about 1.1:1.0 to about 1.0:1.0 and preferably about 1.05:1.0, in the presence of an ether solvent such as tetrahydrofuran (THF) and in the absence of water to form:

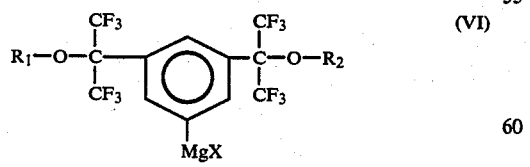

A preferred starting compound (V) is the diether iodide wherein $R_1$ and $R_2$ are each $CH_3$ and X is I; the diether iodide is prepared in accordance with the method described in U.S. Pat. No. 3,879,430 (O'Rear et al.). Preparation of the Grignard reagent (I) is carried out in the complete absence of water, at a temperature of from about 65° to about 68° C., at a time of from about 60 to about 180 minutes, in an atmosphere of argon and at a pressure of from about 1 atmosphere. Preferably the reaction is carried out at 66°-67° C. for about 2 hours.

Instead of a Grignard reagent (Z is MgX), a lithium derivative (Z is Li) may be used. Lithium derivatives are prepared similarly to Grignard reagents—for example see the preparation of lithium derivatives from butyl lithium described in L. Fisher et al., "Reagents For Organic Synthesis," pp. 571–572, Library of Congress Catalogue No. 66-27894. Lithium derivatives are somewhat more reactive than Grignard reagents and thus are more difficult to work with. The Grignard reagents are therefore preferred.

To prepare the diether ol (II), the non-isolated Grignard reagent is reacted with a compound selected from the group consisting of hexafluoroacetone (HFA), bis(perfluoroethyl)ketone, bis(perfluoropropyl)ketone, bis(1,1-dihydroperfluoroethyl)ketone, and bis(1,1,2,2-tetrahydroperfluoropropyl)ketone, in a mole ratio of from about 2.5:1.0 to about 2.0:1.0, preferably about 2.0:1.0. The reaction is carried out at a temperature of from about 20° to about 50° C., at a time of from about 2 to about 4 hours, at a pressure of about 1 atmosphere and in the presence of an ether solvent such as tetrahydrofuran (THF). The resulting intermediate is then hydrolyzed with a dilute acid to form the diether ol. A suitable dilute acid is 4 N hydrochloric acid. The acid should be added in an amount no greater than about 1.1 equivalent. Recovery of the diether ol is effected by conventional means, such as separating the organic layer and subjecting it to distillation.

To prepare the diether acrylate or monomer (IV), the diether ol (II) is reacted with an acrylic compound in a mole ratio of from about 1.1:1.0 to about 1.0:1.0, and preferably about 1.0:1.0, in the presence of an adjuvant such as triethylamine and in an inert organic solvent such as Freon 113. The acrylic compound has the formula:

wherein X' is selected from the group consisting of chlorine and bromine. The purpose of the adjuvant is to promote esterification by acting as an acid acceptor. The reaction is carried out at a temperature of from about 10° to about 20° C., at a time of from about 2 to about 3 hours, in an atmosphere which excludes moisture and at a pressure of about 1 atmosphere. Recovery and purification of the resulting acrylate ester may be effected by conventional procedures. For example, the reaction mixture may be filtered to remove triethylammonium chloride, the filtrate percolated through neutral alumina to remove polar impurities, and the effluent concentrated to yield the ester.

In the preferred process of making the monomer (IV), diether iodide ($R_1$ and $R_2$ are each $CH_3$ and X is I) is reacted with magnesium in the presence of tetrahydrofuran (THF) and in the absence of water to form the Grignard reagent (I). The Grignard reagent is reacted with hexafluoroacetone in the presence of THF and then hydrolyzed with a dilute acid to form the diether ol (II). The diether ol is reacted with acryloyl chloride (III) in the solvent Freon 113 and in the presence of triethylamine as an adjuvant to form the diether acrylate monomer (IV). The monomer is then polymerized in the presence of benzoyl peroxide.

The following examples are set forth primarily for the purpose of illustration and the specific enumeration should not be construed as a limitation on the concept of the invention.

EXAMPLES

EXAMPLE 1

The following materials were employed in this example for the preparation of the monomer (IV): tetrahydrofuran (THF) from Fisher Scientific, Co., Pittsburgh, Pennsylvania, which was dried over Type 13X molecular sieves; acryloyl chloride from Aldrich Chemical Co., Inc., Milwaukee, Wisconsin, distilled prior to use (bp 73°–75° C., 99% purity by GLC); triethylamine (99% min. purity by GLC) from Eastman Kodak Co., Rochester, New York, which was dried over Type 13X molecular sieves; hexafluoroacetone (HFA) from PCR Inc., Gainesville, Florida; and Freon 113 from E. I. DuPont de Nemours & Co., Wilmington, Delaware.

Preparation of 1,3-bis-(2-methoxyhexafluoro-2-propyl)-5-iodobenzene, (V)

The two-step synthesis involved the direct iodination of 1,3-bis-(hydroxyhexafluoro-2-propyl) benzene to obtain 1,3-bis-(2-hydroxyhexafluoro-2-propyl)-5-iodobenzene and the subsequent methylation of the latter to (V); bp 97°–99° C./2.0 mm Hg; $n_D^{20}$ 1.4380; 99.9% purity by GLC.

Preparation of 1,3-bis-(2-methoxyhexafluoro-2-propyl)-5-magnesium-iodobenzene, (I)

To ensure the exclusion of water during preparation of this Grignard reagent, all glassware was baked overnight at 160° C., assembled hot, and protected from the admission of atmospheric moisture by the use of dry argon and/or drying tubes.

0.88 g (0.036 g atom) of magnesium and 50 ml of tetrahydrofuran (THF) were placed in a 3-neck flask equipped with a water-cooled condenser, dropping funnel, thermometer and argon bleed exiting through the condenser. The dropping funnel was charged with a mixture of 20.00 g (0.0355 mole) of the diether iodide (V) and 50 ml of THF. Reaction was initiated by adding 15 ml of the THF-diether iodide mixture and gently heating the magnetically stirred mixture to reflux (external heating bath, 78° C.). Reaction was indicated by clouding after 30 minutes and formation of a white precipitate. The remainder of the THF-diether iodide mixture was added to the stirred, refluxing mixture during another hour. Stirring and slow refluxing for another 1½ hours left a copious white precipitate and a few fragments of unreacted magnesium. The Grignard mixture was then cooled to 20° C. for the next step.

Preparation of 1,3-bis-(2-methoxyhexafluoro-2-propyl)-5-(2-hydroxyhexafluoro-2-propyl)-benzene, (II)

To react the Grignard reagent with hexafluoroacetone (HFA), the water-cooled condenser was replaced by a dry ice-acetone condenser terminated with a drying tube (CaCl$_2$), and the dropping funnel was replaced by a gas inlet tube connecting with the condensed HFA (11.8 g; 6.3 ml). Distillation of HFA into the stirred reaction mixture during 20 minutes gave a mild exotherm (30°–50° C.). This mixture was stirred another hour and then allowed to stir and vent overnight through the drying tube.

The HFA adduct was hydrolyzed with 30 ml of 4 N hydrochloric acid and diluted with 50 ml of water. The heavy oil was separated and dissolved in 200 ml of ether. The ether extract was washed with a saturated sodium chloride solution, dried and concentrated to 22 g. Distillation of the crude product removed 3 g of THF and (CF$_3$)$_2$CHOH:THF. The 1:1 complex arose from the reduction of some hexafluoroacetone in THF. The remaining 19 g (bp 105°–107° C./10 mm Hg; mp 58°–63° C.) analyzed 3.5% of the diether 1,3-bis(2-methoxyhexafluoro-2-propyl)benzene, 95% of the diether ol (II), 1.5% unreacted diether iodide (V), together with traces of the 1:1 complex. Recrystallizations from petroleum ether (bp 38°–50° C.) (60 ml and 125 ml) at −70° C. removed the diether and diether iodide (V), leaving 17.3 g of white crystals (mp 70° C.) analyzing 99% of the diether ol (II) and containing traces of the 1:1 complex. To remove the 1:1 complex, the latter crystals were stirred and melted in 300 ml of concentrated sulfuric acid at 80° C. for 10 min.; on cooling the floating oil crystallized. Filtration, water washing and drying led to analytical (II) as white crystals; 77.4% yield; mp 72°–73° C.; 100% purity by GLC. By analysis as calculated for C$_{17}$H$_{10}$F$_8$O$_3$: C, 33.79; H, 1.67; F, 56.60; as found: C, 33.56; H, 1.67; F, 56.92.

Preparation of 1,3-bis-(2-methoxyhexafluoro-2-propyl)-5-(2-hydroxyhexafluoro-2-propyl)-benzene acrylate, (IV)

A solution of 14.00 g (0.232 mole) 1,3-bis-(2-methoxyhexafluoro-5-(2-hydroxyhexafluoro-2-propyl)-benzene (II) in 40 ml of Freon 113 was stirred magnetically in a 200 ml 3-neck flask equipped with a dropping funnel, thermometer, dry ice-acetone condenser and drying tube (CaCl$_2$). 24.6 g of triethylamine dissolved in 15 ml of Freon 113 was added dropwise during 20 minutes with slight exotherm. An external cooling bath (ice water) was applied. Then a second dropping funnel charged with 2.20 g (0.024 mole) of acryloyl chloride (III) dissolved in 15 ml of Freon 113 was quickly substituted in place of the empty funnel. The latter charge was added during 30 minutes at 10°–20° C. After stirring an additional 2 hours, the resulting white slurry was vacuum filtered (60 ml C filter - 3 g of Celite cake). Flash evaporation of the filtrate left 15.5 g of honey-like residue that readily crystallized (mp 58°–62° C.) and analyzed 80 mole % diether acrylate (IV), 17% unreacted diether ol (II), and 3% acrylic anhydride. Trituration of this mixture in 100 ml of a 2% sodium hydroxide solution followed by neutralization led to 13.1 g of white crystals (mp 61°–62° C.) analyzing 90.6% (IV) and 9.4% (II), with no acrylic anhydride. The 13.1 g of crude ester was submitted again to the customary esterification procedure using 1.21 g of triethylamine and 1.07 g of acryloyl chloride. This led to 12.9 g of crystals analyzing 94.3 mole % (IV) and 5.7% acrylic anhydride. Workup in 2% sodium hydroxide solution led to 12.6 g of white crystals (mp 65°–66° C.) of 100% purity (IV) by GLC. Recrystallization from petroleum ether at −70° F. (−57° C.) gave 11.7 g analytical (IV) as extremely water repellent white crystals; 76.7% yield; mp 66° C. By analysis as calculated for C$_{20}$H$_{12}$F$_{18}$O$_4$: C, 36.49; H, 1.84; F, 51.95; as found: C, 36.58; H, 1.79; F, 51.96.

EXAMPLE 2

The monomer (IV) synthesized according to the procedure of Example 1 was polymerized in bulk at 85° C. with benzoyl peroxide as a catalyst and in an atmosphere of nitrogen at a pressure of 1 atmosphere. The resulting water-clear plastic was somewhat brittle, soluble in highly fluorinated solvents and capable of producing films of 91° water contact angle.

Having described the invention in detail, those skilled in the art will appreciate that numerous modifications may be made thereof without departing from the spirit of the invention. Therefore, it is not intended that the scope of the invention be limited to the specific embodiment illustrated and described. Rather, it is intended that the scope of the invention be determined by the appended claims and their equivalents.

What is claimed is:

1. A compound comprising a fluoroacrylate ester of the formula:

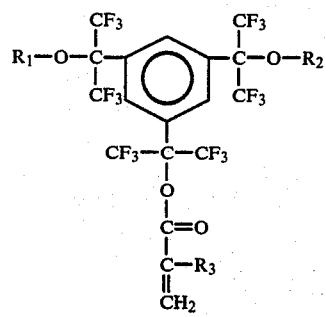
(IV)

wherein $R_1$ and $R_2$ are independently selected from the group consisting of saturated aliphatic hydrocarbons having from 1 to about 3 carbon atoms and $R_3$ is selected from the group consisting of hydrogen and methyl.

2. The compound of claim 1 wherein $R_1$ and $R_2$ are each methyl and $R_3$ is hydrogen.

3. A compound comprising a polymer obtained by polymerizing a fluoroacrylate ester of the formula:

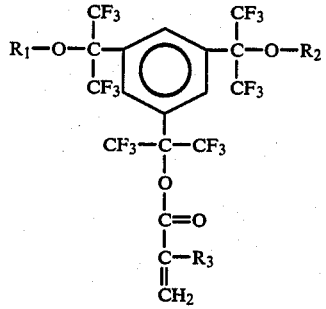
(IV)

wherein $R_1$ and $R_2$ are independently selected from the group consisting of saturated aliphatic hydrocarbons having from 1 to about 3 carbon atoms and $R_3$ is selected from the group consisting of hydrogen and methyl.

4. The polymer of claim 3 having a molecular weight of from about 6,000 to about 60,000.

5. The polymer of claim 4 having a molecular weight of from about 6,000 to about 10,000.

6. An article having a hydrophobic coating comprising the polymer of claim 3.

7. A process for making a fluoroacrylate ester of the formula:

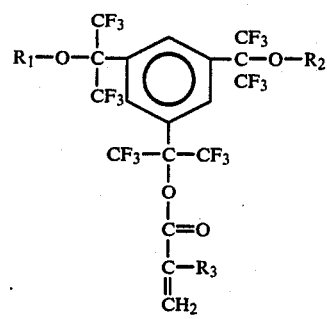

wherein $R_1$ and $R_2$ are independently selected from the group consisting of saturated aliphatic hydrocarbons having from 1 to about 3 carbon atoms and $R_3$ is selected from the group consisting of hydrogen and methyl, said process comprising the steps of:

reacting a compound of the formula:

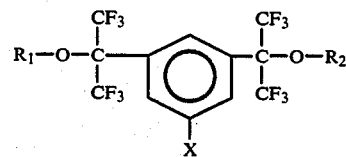
(V)

wherein X is a halogen with magnesium in the presence of an ether solvent and in the absence of water to form a first intermediate of the formula:

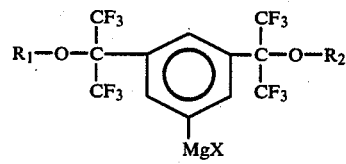
(VI)

reacting said first intermediate with hexafluoroacetone and hydrolyzing the resulting intermediate with a dilute acid to form a second intermediate of the formula:

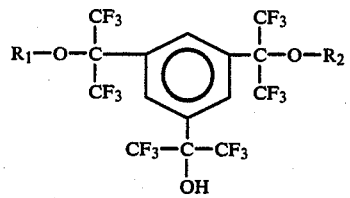
(II)

reacting said second intermediate with an acrylic compound of the formula:

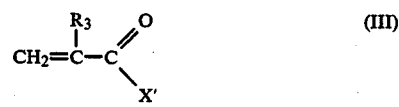
(III)

wherein X' is selected from the group consisting of chlorine and bromine, in the presence of an adjuvant and in an inert organic solvent to form said fluoroacrylate ester.

8. A process for making a fluoroacrylate ester compound of the formula:

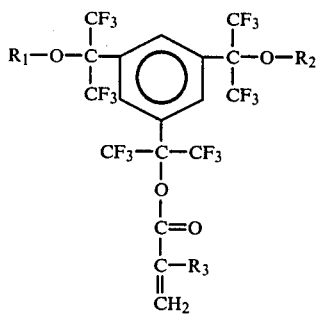

wherein $R_1$ and $R_2$ are independently selected from the group consisting of saturated aliphatic hydrocarbons having from 1 to about 3 carbon atoms and $R_3$ is selected from the group consisting of hydrogen and methyl, said process comprising the steps of:

reacting hexafluoroacetone with a first compound of the formula:

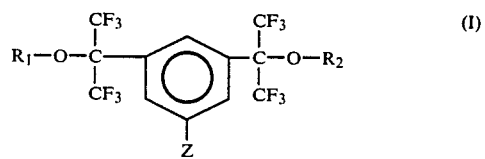

wherein Z is selected from the group consisting of lithium and MgX, where Mg is magnesium and X is a halogen, and hydrolyzing the resulting intermediate with a dilute acid to form a diether ol of the formula:

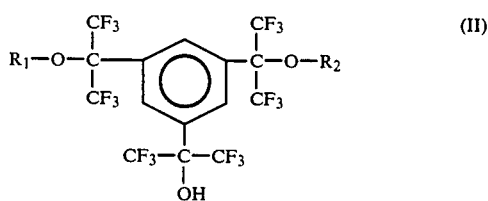

reacting said diether ol with an acrylic compound of the formula:

wherein X' is selected from the group consisting of chlorine and bromine, in the presence of an adjuvant and in an inert organic solvent to form said fluoroacrylate ester compound.

* * * * *